United States Patent
Mori et al.

(10) Patent No.: US 9,504,215 B2
(45) Date of Patent: Nov. 29, 2016

(54) CYTOPLASMIC MALE STERILE EUSTOMA AND A METHOD FOR DEVELOPING THEREOF

(71) Applicant: Sakata Seed Corporation, Kanagawa (JP)

(72) Inventors: Kazutoshi Mori, Kanagawa (JP); Atsushi Izumida, Kanagawa (JP); Shingo Horiuchi, Kanagawa (JP); Takao Suzuki, Kanagawa (JP)

(73) Assignee: SAKATA SEED CORPORATION, Kanagawa (JP)

( * ) Notice: Subject to any disclaimer, the term of this patent is extended or adjusted under 35 U.S.C. 154(b) by 0 days.

(21) Appl. No.: 14/431,913

(22) PCT Filed: Sep. 26, 2013

(86) PCT No.: PCT/JP2013/005722
§ 371 (c)(1),
(2) Date: Mar. 27, 2015

(87) PCT Pub. No.: WO2014/050116
PCT Pub. Date: Apr. 3, 2014

(65) Prior Publication Data
US 2015/0272020 A1    Oct. 1, 2015

(30) Foreign Application Priority Data

Sep. 27, 2012  (JP) ................................ 2012-213296

(51) Int. Cl.
*A01H 1/02* (2006.01)
*A01H 5/02* (2006.01)
*A01H 4/00* (2006.01)
*C07K 14/415* (2006.01)
*C12N 15/82* (2006.01)

(52) U.S. Cl.
CPC ........ *A01H 5/02* (2013.01); *A01H 1/02* (2013.01); *A01H 4/005* (2013.01); *C07K 14/415* (2013.01); *C12N 15/8289* (2013.01)

(58) Field of Classification Search
None
See application file for complete search history.

(56) References Cited

U.S. PATENT DOCUMENTS

2003/0110539 A1    6/2003    Sase

FOREIGN PATENT DOCUMENTS

| CN | 1844370 A | 10/2006 |
|---|---|---|
| CN | 101836587 A | 9/2010 |
| JP | 09-107829 A | 4/1997 |
| JP | 2001-136853 A | 5/2001 |
| JP | 2004-103 A | 1/2004 |
| JP | 4133011 B2 | 6/2008 |
| JP | 2009-165494 A | 7/2009 |
| WO | 0025575 A1 | 5/2000 |

OTHER PUBLICATIONS

Riseman et al. International Journal of Plant Sciences 167(2): 191-199 (Mar. 2006).*
Morgan, E. New Zealand Journal of Crop and Horticultural Science 32(4): 343-347 (Dec. 2004).*
Morgan et al. Acta Horticulturae 836: 97-103 (Aug. 2009).*
Semeniuk et al. Plant Cell, Tissue and Organ Culture 8(3): 249-253 (Jan. 1987).*
Ma et al. Journal of Tropical and Subtropical Botany 10(2): 152-160 (2002) Abstract Only.*
Wise et al. Proc. Natl. Acad.Sci. USA 84: 2858-2862 (1987).*
Skirvin et al. HortScience 29(11): 1232-1237 (1994).*
Iwabuchi, M., "The Molecular Mechanism of Cytoplasmic Male Sterility," Plant Cellular Engineering, vol. 5, No. 4, p. 319, 1993 (with English translation thereof).
Nogyo Gijutsu Taikei (Agricultural Technology System (in Japanese)), "Basic Cultivation," Flowers and Ornamental Plants, vol. 8, addendum, No. 6, pp. 387-395, 2004, issued by Rural Culture Association Japan (with English translation thereof).
Okada, K. et al., "Useful genetically transformed plants awaiting their turn," Tissue Culture (in Japanese), vol. 19, No. 2, pp. 50-55, 1993, New Science Co., Ltd. (with English translation thereof).
Ohkawa, K., Jissen Kaki Engei Gijutsu (Actual Practice of Ornament Horticultural Techniques (in Japanese)), Cultivation Management and Blooming Adjustment of Lisianthus, pp. 6-23, 2003, issued by Seibundo Shinkosha Publishing Co., Ltd. (with English translation thereof).
Mousavi, E.S. et al."Callus Induction and Plant Regeneration in Lisianthus (Eustoma Grandiflorium)," 10th Anniversary Edition Trakia Journal of Sciences, vol. 10, No. 1, pp. 22-26, 2012.
Duminil, J. et al., "A set of 35 consensus primer pairs amplifying genes and introns of plant mitochondrial DNA," Molecular Ecology Notes, vol. 2, p. 428-430, 2002.
Tsunoda, S. et al., Plant Breeding, pp. 114-117 and 194-195, 1991 (with partial English translation thereof).
Itabashi, E. et al., "Plant Cytoplasmic Male Sterility and Fertility Control by Nuclear Genes," Bulletin of the Faculty of Agriculture, Niigata University, vol. 64, No. 2, pp. 135-142, Mar. 2012 (with English translation thereof).
International Search Report for corresponding PCT/JP2013/005722, mailed Dec. 17, 2013 (English translation of ISR included).

(Continued)

*Primary Examiner* — David T Fox

(74) *Attorney, Agent, or Firm* — Pearne & Gordon LLP

(57) ABSTRACT

The present invention relates to a novel *Eustoma* having cytoplasmic male sterility and a method for breeding the same. More specifically, the present invention relates to a novel *Eustoma* having cytoplasmic male sterility, wherein the *Eustoma* substantially lacks pollen production functions due to insufficient stamen or pollen formation, and a method for breeding the same.

27 Claims, 3 Drawing Sheets

(56) References Cited

OTHER PUBLICATIONS

Koncz, et al. "T-DNA Insertional Mutagenesis in Arabidopsis," Plant Molecular Biology, Springer, Dordrecht, NL, vol. 20, No. 5, Jan. 1, 1992, p. 963-976.

Chaudhury, et al. "Genetic control of male fertility in higher plants," Australian Journal of Plant Physiology, CSIRO, Melbourne, AU, vol. 19, No. 4, Jan. 1, 1992, p. 419-426.

Handa, et al. "Genetic transformation of eustoma grandiflorum with ROL genes," Acta Horticulturae, International Society for Horticultural Science, BE, vol. 392, Mar. 1, 1995, p. 209-218.

Extended European Search Report for related European Appl. No. 13841979.1, corresponding to PCT/JP2013/005722, issued Mar. 16, 2016.

Chinese Office Action and Search Report dated Mar. 2, 2016 for Chinese Application No. 20138050323.5.

* cited by examiner (A) SEQ ID NO: 1 (Marker 1) The underlined regions represent primer sites designed for the present invention.

<u>CTACTGAATCCAAGCGAGTGG</u>AATACTTGGAGCGAGCGAGGAGCGAGTGGAATACTTGGAGCGAGCG
AGGAGCGAGTGGAATACTTGGAGCGAGCGAGGAGCGAGTGGAATACTTGGAGCGAGCGAGGAGCGAG
TGGAATGAACGAAAAACCTAAGAAAATCAACTTCAATCAGTGAGCTAGATGAGAAAGGAGACTGAAG
AAACTGAAAGAGTAGTAGGAGGATGAAAAAGGAAGCAAGTGGAGTAGGAGCGAACGTGGGAGTAGGA
AACCCGCTTCCTTTCTTACCCTAAACCCACTTCC<u>TTTCTCGCCCAGCTCTACCTA</u>

(B) SEQ ID NO: 2 (Marker 2) The underlined regions represent primer sites designed for the present invention.

<u>AACCACTAACACCTTCCTCGTTGGGGCTCCGTGCACTGGGAAAACGCTAACGCGACGTTTTTAACTA</u>
GAGTTACAAAGCTCCAATAAGGTATCGAGAGGGCTATCATCGAGAGGAAGCGAGTTCCATACTTGAA
ACGAGCATGGGAGCGAGCGGAGTACTTTCAGCGAGCCTAAAAAGCGAGTTCCATACTCCCATGTTCG
CTCCAGGTGTTCCGCTCACTTGGAACGAAAAACCTAAGAAAATCAACTTCAATCAGTGAGCTAGATG
AGAAAGGAGACTGAATCAACATCAAGAGTAGTAGGTTTGAGAGGATGAGAAGGTAACCGAAGAAAAG
AAAAAAAATCAGTGAGCTAGATGAGAATTAGGAAAAGAGACTTGATCTTATTCAATCAGTGATGAGA
AAGGAGCAAGTGGAGAATCAACATAAATCGAAGTAGAGTGAGCTAGATGAGAAAGGAGACTGAAG<u>AA
ACTTCAAGATACGTAGATAGAGC</u>

Figure 3

SEQUENCE LISTING

```
<160> NUMBER OF SEQ ID NOS: 12

<210> SEQ ID NO 1
<211> LENGTH: 323
<212> TYPE: DNA
<213> ORGANISM: Unknown
<220> FEATURE:
<223> OTHER INFORMATION: Marker 1

<400> SEQUENCE: 1
ctactgaatc caagcgagtg gaatacttgg agcgagcgag gagcgagtgg aatacttgga      60
gcgagcgagg agcgagtgga atacttggag cgagcgagga gcgagtggaa tacttggagc     120
gagcgaggag cgagtggaat gaacgaaaaa cctaagaaaa tcaacttcaa tcagtgagct     180
agatgagaaa ggagactgaa gaaactgaaa gagtagtagg aggatgaaaa aggaagcaag     240
tggagtagga gcgaacgtgg gagtaggaaa cccgcttcct ttcttaccct aaacccactt     300
cctttctcgc ccagctctac cta                                             323

<210> SEQ ID NO 2
<211> LENGTH: 492
<212> TYPE: DNA
<213> ORGANISM: Unknown
<220> FEATURE:
<223> OTHER INFORMATION: Marker 2

<400> SEQUENCE: 2
```

```
aaccactaac accttcctcg ttggggctcc gtgcactggg aaaacgctaa cgcgacgttt    60
ttaactagag ttacaaagct ccaataaggt atcgagaggg ctatcatcga gaggaagcga   120
gttccatact tgaaacgagc atgggagcga gcggagtact ttcagcgagc ctaaaaagcg   180
agttccatac tcccatgttc gctccaggtg ttccgctcac ttggaacgaa aaacctaaga   240
aaatcaactt caatcagtga gctagatgag aaaggagact gaatcaacat caagagtagt   300
aggtttgaga ggatgagaag gtaaccgaag aaaagaaaaa aaatcagtga gctagatgag   360
aattaggaaa agagacttga tcttattcaa tcagtgatga gaaggagca agtggagaat    420 caacataaat cgaagtagag tgagctagat gagaaaggag actgaagaaa cttcaagata   480
cgtagataga gc                                                       492
```

\<210\> SEQ ID NO 3  
\<211\> LENGTH: 21  
\<212\> TYPE: DNA  
\<213\> ORGANISM: Artificial Sequence  
\<220\> FEATURE:  
\<223\> OTHER INFORMATION: primer

\<400\> SEQUENCE: 3

```
ctactgaatc aagcgagtg g                                               21
```

\<210\> SEQ ID NO 4  
\<211\> LENGTH: 20  
\<212\> TYPE: DNA  
\<213\> ORGANISM: Artificial Sequence  
\<220\> FEATURE:  
\<223\> OTHER INFORMATION: primer

\<400\> SEQUENCE: 4

```
taggtagagc tgggcgagaa                                                20
```

\<210\> SEQ ID NO 5  
\<211\> LENGTH: 21  
\<212\> TYPE: DNA  
\<213\> ORGANISM: Artificial Sequence  
\<220\> FEATURE:  
\<223\> OTHER INFORMATION: primer

\<400\> SEQUENCE: 5

```
aaccactaac accttcctcg t                                              21
```

\<210\> SEQ ID NO 6  
\<211\> LENGTH: 26  
\<212\> TYPE: DNA  
\<213\> ORGANISM: Artificial Sequence  
\<220\> FEATURE:  
\<223\> OTHER INFORMATION: primer

\<400\> SEQUENCE: 6

```
gctctatcta cgtatcttga agtttc                                         26
```

\<210\> SEQ ID NO 7  
\<211\> LENGTH: 20  
\<212\> TYPE: DNA  
\<213\> ORGANISM: Artificial Sequence  
\<220\> FEATURE:  
\<223\> OTHER INFORMATION: primer

\<400\> SEQUENCE: 7

```
ctgtyttttc gcacttaggc                                                20
```

-continued

```
<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gtccgrggta ctattgctgt                                                 20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgtcctccat cacgatvtcg                                                 20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ccaaattctc ctttaggtgc                                                 20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ccaatttttg ggccaattcc                                                 20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
cattgcaaag gcataatgat                                                 20
```

CYTOPLASMIC MALE STERILE EUSTOMA AND A METHOD FOR DEVELOPING THEREOF

TECHNICAL FIELD

The present invention relates to a novel *Eustoma* having cytoplasmic male sterility and a method for breeding the same. More specifically, the present invention relates to a novel *Eustoma* having cytoplasmic male sterility, wherein the *Eustoma* substantially lacks pollen production functions due to insufficient stamen or pollen formation, and a method for breeding the same.

BACKGROUND ART

*Eustoma* is a generic name for autogamous seed-propagated plants of the genus *Eustoma* in the family Gentianaceae and grows natively in regions of southern North America to northern Central America. These plants include two species: (1) *Eustoma grandiflorum* (English name: Prairie gentian, former scientific name: *E. russellianum* (Hook) G. Don ex Sweet or *Lisianth(i)us russellianus* Hook.) and (2) *Eustoma exaltatum* (English name: Seaside gentian or Catchfly gentian, former scientific name: *E. selenifolium* Salisb.). The plants are also known familiarly as *Lisianthus*. In 1835, the native species was brought to Scotland and designated as *Lisianthus russellianus* Hook. The plants were introduced to Japan in the 1930s and have been actively bred since then, mainly for cut flowers or potted plants. *Eustoma grandiflorum* is mainly used in such breeding.

*Eustoma* is known for flowers and ornamental plants of high ornamental and market value. Particularly, varieties having diverse characters have been produced as varieties for cut flowers, and these *Eustoma* varieties are regarded as one of the principal cut flower species (see Non Patent Literature 1).

In general, first filial generation (F1) plants superior in character to their parents are utilized in major horticultural crops because of the benefits from heterosis. Among *Eustoma* cultivars highly demanded as cut flowers, first filial generation varieties are also the mainstream because this allows the plants to have disease resistance or high quality.

For efficient seeding in plant production, breeders are required to supply highly pure seeds. The seed production of a first filial generation variety first involves manual emasculation of a seed parent followed by pollinating the stigma of the emasculated seed parent with the pollen of a pollen parent.

The period when a flower of the seed parent can be successfully emasculated is usually limited to a stage immediately before flowering, and also tends to depend on weather conditions. The emasculation therefore presents operation problems in that the possible period of emasculation is rarely predictable. Since this operation is manually performed, pollen that has remained due to insufficient emasculation may cause the emergence of unintended self-pollinated seeds. Contamination by such self-pollinated seeds results in unfavorable reduction in the quality of seeds. For these reasons, there has been a demand for the development of a method for seed production of *Eustoma* by use of male sterility that eliminates the need of the manual emasculation of seed parents.

Dwarf *Lisianthus* transformed by rolC gene transfer using *Agrobacterium rhizogenes* is known (Non Patent Literature 2), which reportedly has small flowers and loses pollen fertility at the same time with the disappearance of apical dominance (rol syndrome). The technique of Non Patent Literature 2 has been applied to a disclosed method for producing an F1 variety using *Lisianthus* having male sterility, wherein the variety is maintained by adventitious shoot regeneration (Patent Literature 1). The F1 variety produced according to the method, however, possesses undesired characters. Therefore, the method cannot be used in the breeding of cut flower varieties required to have marketable plant postures or heights.

Cytoplasmic male sterility (CMS), one type of male sterility, is cytoplasmically inherited. The crossing of a cytoplasmic male sterile line with a male fertile line supplies highly pure seeds. In addition, the cytoplasmic male sterile line can be crossed with a maintainer line having the same nuclear genome as that of the cytoplasmic male sterile line and a normal cytoplasm to thereby easily maintain and propagate the line. Thus, such a method for seed production of a first filial generation variety by use of cytoplasmic male sterility is very highly practical and is used in a large number of major horticultural crops. Nonetheless, a method for producing a cytoplasmic male sterile *Eustoma* has not yet been reported, though the development of the method for seed production of *Eustoma* by use of male sterility has been demanded. Accordingly, seed production that requires emasculation operation is still performed in the seed production of *Eustoma* F1 varieties due to the absence of a seed production system using practical male sterile lines.

Meanwhile, good flower shelf life that achieves the prolonged ornamental period of flowers resulting from delayed petal aging has been demanded. Examples of causes of petal aging include pollination and ethylene formation caused by damage on the stigma or style of a pistil (Non Patent Literature 3).

*Eustoma* having a deformed pistil, the stigma of which is kept closed to thereby prevent pollination and delay flower aging is known as a *Eustoma* variety having good flower shelf life (Patent Literature 2).

Improvement in flower shelf life has required breeding a line having short filaments of stamens, or using a plant line having an organ structure changed to prevent pollination on its stigma physically, as in the deformed pistil mentioned above.

As one condition, the prevention of pollen dispersion has been demanded for flowers and ornamental plants of high market value. All current *Eustoma* varieties, however, have stamens that produce pollen and therefore cause, for example, pollen dispersion, which is unfavorable due to the fouling of petals or clothing.

Although problems associated with flower shelf life, etc. can be solved by use of male sterility, without changing useful characters, such a practical *Eustoma* having male sterility has not yet been developed.

CITATION LIST

Patent Literature

[Patent Literature 1] Japanese Patent Laid-Open No. 9-107829
[Patent Literature 2] Japanese Patent No. 4133011

Non Patent Literature

[Non Patent Literature 1] Nogyo Gijutsu Taikei (Agricultural Technology System (in Japanese)), Flowers and Ornamental Plants, Vol. 8, addendum, No. 6, p. 387-395, 2004, issued by Rural Culture Association Japan

[Non Patent Literature 2] The Tissue Culture (in Japanese), Vol. 19, No. 2, p. 50-55, 1993, New Science Co., Ltd.

[Non Patent Literature 3] Jissen Kaki Engei Gijutsu (Actual Practice of Ornament Horticultural Techniques (in Japanese)), Cultivation Management and Blooming Adjustment of *Lisianthus*, 2003, issued by Seibundo Shinkosha Publishing Co., Ltd.

[Non Patent Literature 4] E. S. Mousavi, M. Behbahani, E. Hadavi, S. M. Miri (2012), CALLUS INDUCTION AND PLANT REGENERATION IN *LISIANTHUS* (*EUSTOMA GRANDIFLORIUM*), ANNIVERSARY EDITION TRAKIA JOURNAL OF SCIENCES, Vol. 10, No. 1, pp. 22-25

[Non Patent Literature 5] J. Duminil, M.-H. PEMONGE and R. J. PETIT (2002), Molecular Ecology Notes, vol. 2, p. 428-430 "A set of 35 consensus primer pairs amplifying genes and introns of plant mitochondrial DNA"

SUMMARY OF INVENTION

Technical Problem

In light of the problems such as cumbersome emasculation during the F1 seed production of conventional *Eustoma* varieties, the problem of reduced seed quality, and challenges to flower shelf life or pollen dispersion as described above, the present invention is to provide a novel *Eustoma* having cytoplasmic male sterility and a method for producing the same.

Solution to Problem

The present inventors have conducted diligent studies to attain the objective and consequently completed a breeding method which involves producing a novel *Eustoma* plant having cytoplasmic male sterility, breeding the *Eustoma* line having cytoplasmic male sterility, and obtaining a first filial generation variety using the cytoplasmic male sterile *Eustoma*.

Specifically, the present invention relates to a novel *Eustoma* having cytoplasmic male sterility and a method for breeding the same. More preferably, the present invention relates to a novel *Eustoma* having cytoplasmic male sterility, wherein the *Eustoma* substantially lacks pollen production functions due to insufficient stamen or pollen formation, and a method for breeding the same.

Specifically, the present invention provides the following (1) to (34):

(1) A *Eustoma* plant having cytoplasmic male sterility, or progeny thereof.

(2) The *Eustoma* plant or progeny thereof according to (1), wherein the *Eustoma* plant or progeny thereof has the nucleotide sequence represented by SEQ ID NO: 1 or 2.

(3) The *Eustoma* plant or progeny thereof according to (1) or (2), wherein the *Eustoma* plant or progeny thereof is a cytoplasmic male sterile plant produced from a cross pollination whose seed parent is a *Eustoma* plant having the nucleotide sequence represented by SEQ ID NO: 1 or 2 and whose pollen parent is an arbitrary *Eustoma* plant.

(4) The *Eustoma* plant or progeny thereof according to any of (1) to (3), wherein the *Eustoma* plant or progeny thereof is a cytoplasmic male sterile plant produced from a cross pollination whose seed parent is the *Eustoma* plant having the nucleotide sequence represented by SEQ ID NO: 1 or 2 and whose pollen parent is *E. grandiflorum*.

(5) A partial plant body of the *Eustoma* plant or progeny thereof according to any of (1) to (4).

(6) A seed of the *Eustoma* plant or progeny thereof according to any of (1) to (4).

(7) A callus comprising cells of the *Eustoma* plant or progeny thereof according to any of (1) to (4).

(8) A *Eustoma* plant that is induced from the callus according to (7) and asexually propagated by tissue culture, or progeny thereof.

(9) A partial plant body of the *Eustoma* plant or progeny thereof according to (8).

(10) A method for preparing a *Eustoma* plant that is induced from the callus according to (7) and asexually propagated by tissue culture.

(11) A cytoplasm contained in the *Eustoma* plant or progeny thereof according to any of (1) to (4) and (8), the partial plant body according to any of (5) and (9), the seed according to (6), or the callus according to (7).

(12) A mitochondrion contained in the *Eustoma* plant or progeny thereof according to any of (1) to (4) and (8), the partial plant body according to any of (5) and (9), the seed according to (6), or the callus according to (7).

(13) A *Eustoma* plant having cytoplasmic male sterility which is designated by Deposition No. FERM BP-11506, or progeny thereof.

(14) A partial plant body of the *Eustoma* plant or progeny thereof according to (13).

(15) A seed of the *Eustoma* plant or progeny thereof according to (13).

(16) A cytoplasm contained in the *Eustoma* plant or progeny thereof according to (13), the partial plant body according to (14), or the seed according to (15).

(17) A mitochondrion contained in the *Eustoma* plant or progeny thereof according to (13), the partial plant body according to (14), or the seed according to (15).

(18) A callus of a *Eustoma* plant having cytoplasmic male sterility which is designated by Deposition No. FERM BP-11507.

(19) A *Eustoma* plant that is induced from the callus according to (18) and asexually propagated by tissue culture, or progeny thereof.

(20) A partial plant body of the *Eustoma* plant or progeny thereof according to (19).

(21) A method for preparing a *Eustoma* plant that is induced from the callus according to (18) and asexually propagated by tissue culture.

(22) A cytoplasm contained in the callus according to (18), the *Eustoma* plant or progeny thereof according to (19), or the partial plant body according to (20).

(23) A mitochondrion contained in the callus according to (18), the *Eustoma* plant or progeny thereof according to (19), or the partial plant body according to (20).

(24) A method for producing a first filial generation seed, comprising crossing the *Eustoma* plant or progeny thereof according to any of (1) to (4) and (8) as a seed parent with a *Eustoma* plant capable of being crossed with the seed parent plant as a pollen parent, and producing a first filial generation seed from the seed parent thus crossed.

(25) A method for producing a first filial generation seed, comprising crossing the *Eustoma* plant or progeny thereof according to (13) as a seed parent with a *Eustoma* plant capable of being crossed with the seed parent plant as a pollen parent, and producing a first filial generation seed from the seed parent thus crossed.

(26) A method for producing a first filial generation seed, comprising crossing a *Eustoma* plant regenerated from the callus according to (18), or progeny thereof as a seed parent with a *Eustoma* plant capable of being crossed with the seed parent plant as a pollen parent, and producing a first filial generation seed from the seed parent thus crossed.

(27) A first filial generation seed produced by the method according to any of (24) to (26).

(28) A first filial generation plant grown from the first filial generation seed according to (27).

(29) A method for producing a *Eustoma* plant, comprising successively back-crossing a *Eustoma* plant having the nucleotide sequence represented by SEQ ID NO: 1 or 2 in its cytoplasm with a *Eustoma* plant having a useful character to produce a *Eustoma* plant that has the useful character and expresses cytoplasmic male sterility.

(30) A method for producing a *Eustoma* plant, comprising successively back-crossing a *Eustoma* plant having cytoplasmic male sterility which is designated by Deposition No. FERM BP-11506, or progeny thereof with a *Eustoma* plant having a useful character to produce a *Eustoma* plant that has the useful character and expresses cytoplasmic male sterility.

(31) A method for producing a *Eustoma* plant, comprising successively back-crossing a *Eustoma* plant that is induced from a callus of a *Eustoma* plant having cytoplasmic male sterility which is designated by Deposition No. FERM BP-11507 and asexually propagated by tissue culture, or progeny thereof with a *Eustoma* plant having a useful character to produce a *Eustoma* plant that has the useful character and expresses cytoplasmic male sterility.

(32) The method for producing a *Eustoma* plant according to any of (29) to (31), wherein the *Eustoma* plant having a useful character is derived from *E. grandiflorum*.

(33) A *Eustoma* plant produced by the method according to any of (29) to (32), or progeny thereof.

(34) A partial plant body of the *Eustoma* plant or progeny thereof according to (33).

Advantageous Effects of Invention

Use of the novel *Eustoma* having cytoplasmic male sterility, provided by the present invention, achieves breeding a *Eustoma* plant and its F1 variety with excellent seed productivity, flower shelf life, and/or ornamental characteristics and producing high-quality seeds of its F1 variety.

BRIEF DESCRIPTION OF DRAWINGS

FIG. 1(A) shows a male fertile line, FIGS. 1(B) and 1(C) show a cytoplasmic male sterile line having imperfectly developed stamens. FIG. 1(D) shows a cytoplasmic male sterile line having no stamen.

FIG. 2(A) shows results obtained using Marker 1 which is a marker specific for the SSE-CMS *Eustoma* line. FIG. 2(B) shows results obtained using Marker 2 which is a marker specific for the SSE-CMS *Eustoma* line. FIG. 2(C) shows results obtained using nad5/4-5 which is a marker common to all *Eustoma* plants.

FIG. 3 shows the nucleotide sequences of Marker 1 and Marker 2.

DESCRIPTION OF EMBODIMENTS

Hereinafter, the present invention will be described in detail.

1. Cytoplasmic Male Sterile *Eustoma*

A method for breeding the *Eustoma* having male sterility of the present invention comprises screening *Eustoma* plant hybrids for a *Eustoma* having cytoplasmic male sterility.

The "*Eustoma* plant" or the "*Eustoma*" according to the present invention refers to a plant of the genus *Eustoma* in the family Gentianaceae. This plant is a horticultural crop known familiarly as *Lisianthus* in Japan.

Figure 1:
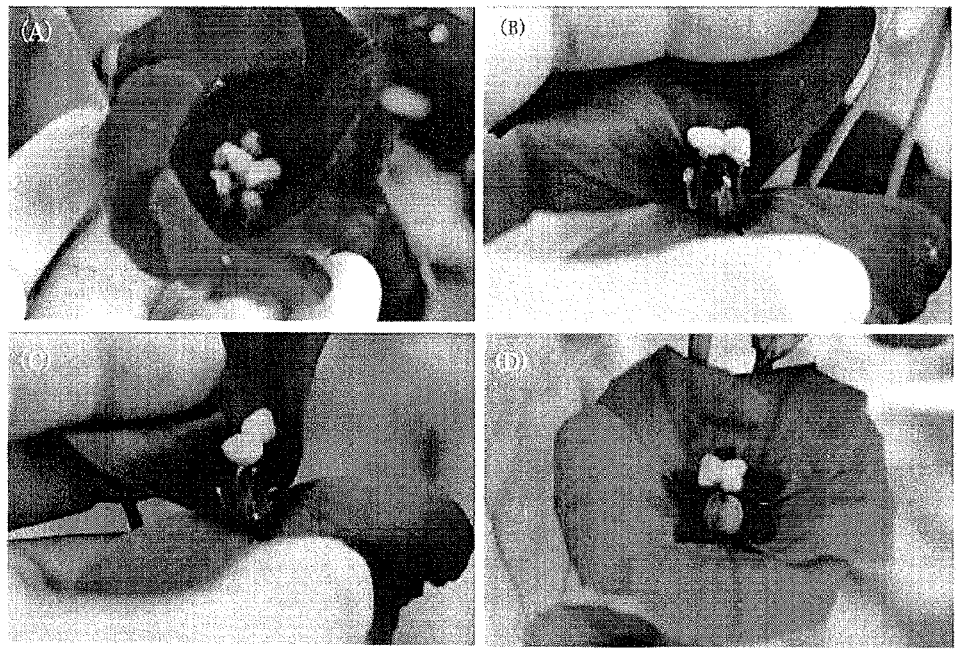
FIG. 1 shows the cytoplasmic male sterile *Eustoma* of the present invention and a male fertile *Eustoma*.

Flowers, including *Eustoma* flowers, usually have sepals and petals within which stamens and pistils are present. Typical stamens consist of pollen-containing anthers and filaments. The "male sterility" according to the present invention refers to the state where imperfectly developed stamens cannot sufficiently produce pollen. The male sterility is exhibited by, but not limited to, for example, a *Eustoma* having no stamen or imperfectly developed stamens (see FIG. 1). The "cytoplasmic male sterility" refers to a male sterile character maternally inherited by an organ-derived gene of the cytoplasm.

In the present invention, the "progeny of a *Eustoma* plant having cytoplasmic male sterility" means a next-generation or later *Eustoma* plant that is obtained by the crossing of a female parent (seed parent) *Eustoma* plant having cytoplasmic male sterility with a male parent (pollen parent) *Eustoma* plant capable of being crossed with the plant and possesses maternally inherited male sterility. In the present invention, the "partial plant body" contains one or more cell(s) of the plant or a cytoplasm from one or more cell(s) of the plant and specifically means any of organs or tissues such as flowers, leaves, stems, and roots, cells (including protoplasts prepared from the cells) or cytoplasms from these organs or tissues, and a population of the cells or the cytoplasms.

In the present specification, the scope of the "*Eustoma* plant which is designated by Deposition No. FERM BP-11506" also includes plants that have the character of cytoplasmic male sterility and are substantially equivalent to the plant. Specifically, the scope of the "*Eustoma* plant which is designated by Deposition No. FERM BP-11506" also includes, for example, mutants or gene recombinants of the *Eustoma* plant designated by Deposition No. FERM BP-11506 as long as the mutants or gene recombinants maintain cytoplasmic male sterility.

In the present specification, the scope of the "callus of a *Eustoma* plant which is designated by Deposition No. FERM BP-11507" also includes calluses from which plants having the character of cytoplasmic male sterility are regenerated and which are substantially equivalent to the callus. Specifically, the scope of the "callus of a *Eustoma* plant which is designated by Deposition No. FERM BP-11507" also includes, for example, mutants or gene recombinants derived from the callus of a *Eustoma* plant which is designated by Deposition No. FERM BP-11507 and calluses derived from mutants or gene recombinants (maintaining cytoplasmic male sterility) of the *Eustoma* plant which is designated by Deposition No. FERM BP-11506, as long as plants regenerated therefrom maintain cytoplasmic male sterility.

The cytoplasmic male sterile *Eustoma* according to the present invention has the following features:
(1) This line eliminates the need for the emasculation of seed parents for the production of a first filial generation variety and therefore achieves economically efficient seed production.
(2) The crossing of this line with a male fertile line supplies highly pure seeds because of its male sterile character.
(3) This line can be crossed with a maintainer line having the same nuclear genome as that of the line and a normal cytoplasm to thereby easily maintain and propagate the line.
(4) This line, which is free from self-pollination, can suppress flower aging caused by pollination, resulting in good flower shelf life.
(5) This line has no pollen and therefore, does not foul petals or clothing by pollen dispersion.

2. Method for Producing Cytoplasmic Male Sterile *Eustoma*

The method for producing a male sterile *Eustoma* according to the present invention involves crossing a wild *Eustoma* plant species as a female parent with *Eustoma grandiflorum* as a male parent, screening individuals that exhibit male sterility among the progeny. An individual having no stamen or imperfectly developed stamens is screened for as the individual that exhibits male sterility. In order to further confirm that the male sterility is a character that is cytoplasmically inherited, the individual is backcrossed with the male fertile *Eustoma* line, and their progeny plants are confirmed to exhibit male sterility.

3. Method for Producing First Filial Generation Seed

The cytoplasmic male sterile *Eustoma* produced by the method of the present invention can be successively backcrossed with a *Eustoma* plant having a preferred character to thereby obtain a preferred line having cytoplasmic male sterility as progeny. This preferred line having cytoplasmic male sterility can be used as a seed parent for obtaining a first filial generation seed (F1 seed).

4. Flower Shelf Life Test

The cytoplasmic male sterile *Eustoma* according to the present invention can be evaluated for its flower shelf life as shown below. In the present specification, the "flower shelf life" means the "duration of flowering". Accordingly, the "good flower shelf life" means a "relatively long flowering period from the start of flowering to the finish of flowering". Whether the flowering period of a *Eustoma* is relatively long is determined by the comparative evaluation of a plurality of respective individuals of the normal male fertile *Eustoma* and the cytoplasmic male sterile *Eustoma* cultivated under the same environmental conditions.

As an example of the flower shelf life test, a method for evaluating the shelf life of a cut flower will be described. In this method, appropriate numbers of normal male fertile individuals and male sterile individuals of *Eustoma* cultivated under the same conditions are first prepared as test materials. The flowers of these *Eustoma* individuals are collected almost simultaneously on the day of flowering (day when the opening of petals is observed) with their peduncles on. The peduncles are adjusted to a constant length (e.g., approximately 4 to 6 cm). Subsequently, the adjusted test materials are left standing in a temperature-controlled room having a constant temperature (preferably 18 to 22° C.), a constant humidity (preferably 55 to 65%), and 12-hour light/12-hour dark cycles such that the cut sections of their stems are dipped in water. Change in the appearance of the flowers is observed.

The "start of flowering" is defined as the time when petals have opened. The "finish of flowering" is determined from the appearance of the petals (shriveling or withering of the petals) to measure the flowering period of each flower (period from the start of flowering to the finish of flowering). The averages of the respective measured flowering periods can be determined and compared between the normal male fertile individuals and the male sterile individuals to evaluate the flower shelf life of the male sterile *Eustoma* of the present invention.

5. Development of Molecular Markers to Distinguish the Cytoplasm

Mitochondrial genomic sequences are compared between the cytoplasmic male sterile *Eustoma* line prepared by the present invention and a conventionally known *Eustoma* plant. A region specific for the cytoplasmic male sterile *Eustoma* line can be identified to thereby prepare a molecular marker serving as a distinguishing factor. The molecular marker can be detected according to a method well known to those skilled in the art, such as PCR. Use of the molecular marker can demonstrate that the cytoplasmic male sterile *Eustoma* line according to the present invention distinctly differs not only in morphological feature but in molecular biological feature from conventionally known *Eustoma* plants.

The nucleotide sequences represented by SEQ ID NOs: 1 and 2 can be used as molecular markers to distinguish the cytoplasmic male sterile *Eustoma* line of the present invention. Alternatively, a *Eustoma* line having a nucleotide sequence derived from the nucleotide sequence represented by SEQ ID NO: 1 or 2 by the deletion, substitution, or addition of one or several base(s) can also be regarded as substantially the same line as the cytoplasmic male sterile *Eustoma* line of the present invention, as long as the nucleotide sequence is amplified and detected in the same way as in the nucleotide sequence of SEQ ID NO: 1 or 2. For example, a nucleotide sequence having 80%, preferably 90%, more preferably 95% or higher homology to the nucleotide sequence represented by SEQ ID NO: 1 or 2 can be used as a molecular marker to distinguish the cytoplasmic male sterile *Eustoma* line.

6. Callus Induction, Propagation, and Redifferentiation of Cytoplasmic Male Sterile *Eustoma* Line The cytoplasmic male sterile *Eustoma* line prepared by the present invention may be asexually propagated by tissue culture. The cytoplasmic male sterile *Eustoma* line can be asexually propagated by, for example, a method for callus induction and redifferentiation disclosed in Non Patent Literature 4.

Specifically, the surface of the leaf disc of the cytoplasmic male sterile *Eustoma* line cultivated in a greenhouse is sterilized, then placed to a callus induction medium, and cultured to induce a callus. Then, the formed callus is transferred to a redifferentiation medium and cultured to induce a shoot. Subsequently, the formed shoot is transferred to a rooting medium to induce rooting. In this way, a plant is regenerated. Those skilled in the art can appropriately set culture conditions for callus induction, propagation, and redifferentiation according to a technique known in the art.

The contents of all patents and references explicitly cited herein are incorporated herein by reference in their entirety. Also, the contents described in the specification and drawings of Japanese Patent Application No. 2012-213296 (filed on Sep. 27, 2012) on which claim for the priority of the present application is based are incorporated herein by reference in their entirety.

EXAMPLES

The present invention will be described specifically with reference to Examples below. However, the present invention is not limited to these Examples by any means.

Example 1

Production of Novel *Eustoma* Plant Having Male Sterility

The *Eustoma* having male sterility of the present invention was produced at the Misato Research Station of Sakata Seed Corporation by screening from hybrids between a native *Eustoma* plant of unidentified species name introduced from the United States of America and *Eustoma grandiflorum*.

Breeding Process of *Eustoma* Plant According to the Present Invention

Approximately 60 sets in total of hybrids were previously prepared between dozen lines of native *Eustoma* plants of unidentified species name retained by Sakata Seed Corporation and parent lines (*E. grandiflorum*) of different origins also retained by Sakata Seed Corporation to obtain F1 seeds. These F1 seeds were sown, and the phenotypes of the F1 plants were checked. Then the F1 populations were screened for two or three appropriate individuals, which were then subjected to mass crossing to obtain progeny (hereinafter, referred to "F2 generation") seeds.

The F2 generation seeds were sown and approximately 50 to 100 individuals were cultivated. Phenotypic characters included in the F2 populations were checked. As a result, the segregation of the diameters, colors, and types of flowers, and earliness was seen in most of the F2 populations. Among these populations, an F2 population derived from F1 seeds (hereinafter, referred to as Set A) obtained by the crossing of a native *Eustoma* plant E-1 of unidentified species name retained by Sakata Seed Corporation as a female parent with a parent line G-1 (*E. grandiflorum*) as a male parent offered, unexpectedly, a plurality of individuals that exhibited a male sterile character that had previously been unknown about *Eustoma* plants. One individual was selected from among these individuals and crossed with 4 parent lines G-2, G-3, G-4, and G-5 retained by Sakata Seed Corporation as pollen parents to obtain progeny seeds (F2BC1 generations; referred to as Sets B, C, D, and E, respectively). The generations are indicated by BC1, BC2, . . . , with respect to the number of backcrosses to *E. grandiflorum* with a CMS (Cytoplasmic male sterile) line in order to avoid confusion.

These progeny seeds (F2BC1 generations) were sown and the characters of 12 individuals per line were checked. As a result, all lines and individuals exhibited a male sterile character with no stamen or imperfectly developed stamens. Four F2BC1-generation individuals derived from Set C (hereinafter, referred to as ms-1), two F2BC1-generation individuals derived from Set D (hereinafter, referred to as ms-2), three and four F2BC1-generation individuals derived from Set E (hereinafter, referred to as ms-3 and ms-4) were selected and crossed with pollen parents, i.e., parent lines G-3 and G-6 for ms-1, parent lines G-4 and G-7 for ms-2, parent lines G-5 and G-8 for ms-3, and parent lines G-5 and G-9 for ms-4 to obtain their respective progeny seeds (F2BC2 generations).

The progeny seeds (F2BC2 generations) were sown, and the phenotypic characters of the progeny were checked. As a result, progeny populations of lines obtained by the crossing of ms-1 with G-3 and G-6 had some male sterile individuals having imperfectly developed stamens, while the other combinations exhibited a male sterile character with no stamen. These male sterile individuals were crossed with approximately 100 parent lines to obtain progeny seeds (F2BC3 generations).

The progeny seeds (F2BC3 generations) were sown and the phenotypic characters of the progeny was examined. As a result, the progeny was confirmed to have a male sterile character. This demonstrated that a cytoplasmic male sterile line exhibiting stable maternal inheritance was successfully produced. Thus, its cytoplasm was designated as an SSE-CMS cytoplasm. The F2BC1 seed exhibiting stable cytoplasmic male sterility was internationally deposited with National Institute of Technology and Evaluation (NITE) International Patent Organisms Depositary (Tsukuba Central 6, 1-1-1 Higashi, Tsukuba, Ibaraki, Japan) on Jul. 20, 2012 (indication given by the depositor for identification: 08P-81S; Deposition No. FERM BP-11506).

Example 2

Validation of Reproducibility of Male Sterility

In order to confirm the stable emergence of the male sterile character, the *Eustoma* plant E-1 was crossed as a female parent with the parent line G-10 (*E. grandiflorum*) as a male parent to produce F1 seeds (hereinafter, referred to as Set F). The seeds of Sets A and F were sown, and 6 individuals per set were selected and subjected to mass crossing. As a result, the individuals derived from Set A produced F2-generation seeds at a yield of 0.22 g for 56 pods, while the individuals derived from Set F produced F2-generation seeds at a yield of 0.47 g for 59 pods. The F2-generation seeds of each set were sown and examined for the rate of emergence of male sterile individuals. As a result, 19 out of 92 F2-generation individuals derived from Set A and 14 out of 88 F2-generation individuals derived from Set F exhibited the male sterile character.

These results showed that the male sterile character emerges stably.

Example 3

Flower Shelf Life Test on *Eustoma* Variety Having Male Sterility

Male sterile lines and fertile lines were subjected to a flower shelf life test.

(1) Test Materials

Two types of *Eustoma* plants were used as test materials: F1 individuals of normal male fertile *Eustoma* and F1 individuals of cytoplasmic male sterile *Eustoma*. The flowers (which all appeared to have started flowering) of these two types of *Eustoma* individuals were collected from a *Eustoma* cultivation field with their peduncles on. The peduncles were adjusted to a length of 4 cm. The stigmas of the male fertile *Eustoma* individuals were hand-pollinated with pollen on the assumption that these individuals would be transported. Also, the cytoplasmic male sterile *Eustoma* individuals were or were not hand-pollinated with the pollen of a male fertile line, and these individuals were both subjected to the test.

(2) Test Method

The flower shelf life test was conducted with each test material put into a test tube filled with tap water and carried out in a temperature-controlled room having a temperature of 20° C., a humidity of 60% (±5%), and 12-hour on/12-hour off cycles of a general fluorescent lamp (I-line White Rapid 40 W). During this test, water was not replaced because pollution, etc., was not particularly observed in the water.

(3) Evaluation and Determination

The "start of flowering" is defined as the time when petals have opened. The "finish of blooming" was determined on the basis of petal appearance (shriveling or withering of flowers) by a breeder.

(4) Test Results

The cytoplasmic male sterile *Eustoma* pollinated with the pollen of a fertile line did not much differ in flower shelf life from the male fertile *Eustoma*. This demonstrated that the test conditions were conditions under which the genetic background of the line used did not influence flower shelf life. Since the cytoplasmic male sterile *Eustoma* produces no pollen, its flower shelf life was as much as 7 days longer on average than that of the male fertile line (Table 1).

As a result, 2 types of molecular markers, "Marker 1" and "Marker 2", which allowed amplification of DNA fragments only from the SSE-CMS *Eustoma* line were successfully developed. Marker 1 is a marker that allows amplification of the 323-bp DNA fragment represented by SEQ ID NO: 1 using primers orf25-F and orf25-R (FIG. 3). Marker 2 is a marker that allows amplification of the 492-bp DNA fragment represented by SEQ ID NO: 2 using primers nad7-F and nad7-R (FIG. 3).

The markers prepared by the approach described above were used to carry out a PCR test using, as templates, 190 existing *Eustoma* lines (*E. grandiflorum*) bred by Sakata Seed Corporation and 34 lines of wild *Eustoma* species retained by Sakata Seed Corporation. As a result, the line carrying these two types of nucleotide sequences was confirmed to be only the SSE-CMS *Eustoma* line. The part of

TABLE 1

Flower shelf life test

| Material | Treatment method | 4 days later | 5 days later | 6 days later | 7 days later | 8 days later | 9 days later | 10 days later | 11 days later |
|---|---|---|---|---|---|---|---|---|---|
| | | The number of individuals at finish of flowering | | | | | | | |
| Male fertile line | Hand-pollination | 12 | 17 | 15 | 9 | 5 | 2 | 1 | |
| Male sterile line | Hand-pollination with pollen derived from fertile line | 3 | 11 | 14 | 10 | 11 | 8 | 3 | |
| Male sterile line | Without pollination | | | | 3 | 3 | 4 | 6 | 7 |

| Material | Treatment method | 12 days later | 13 days later | 14 days later | 15 days later | 16 days later | 17 days later | 18 days later | The total number of examined individuals | The average days until finish of flowering |
|---|---|---|---|---|---|---|---|---|---|---|
| | | The number of individuals at finish of flowering | | | | | | | | |
| Male fertile line | Hand-pollination | | | | | | | | 61 | 5.8 |
| Male sterile line | Hand-pollination with pollen derived from fertile line | | | | | | | | 60 | 6.9 |
| Male sterile line | Without pollination | 6 | 8 | 5 | 5 | 2 | 4 | 7 | 60 | 12.8 |

Example 4

Development of Molecular Markers to Distinguish SSE-CMS *Eustoma* Line

The SSE-CMS *Eustoma* line produced by the present invention exhibited a phenotypic feature that was not found in conventional cultivars or wild species. Meanwhile, a molecular marker to distinguish the SSE-CMS *Eustoma* line was prepared in order to demonstrate that this line also differed from conventionally known *Eustoma* plants from the standpoint of molecular biology.

Figure 2:
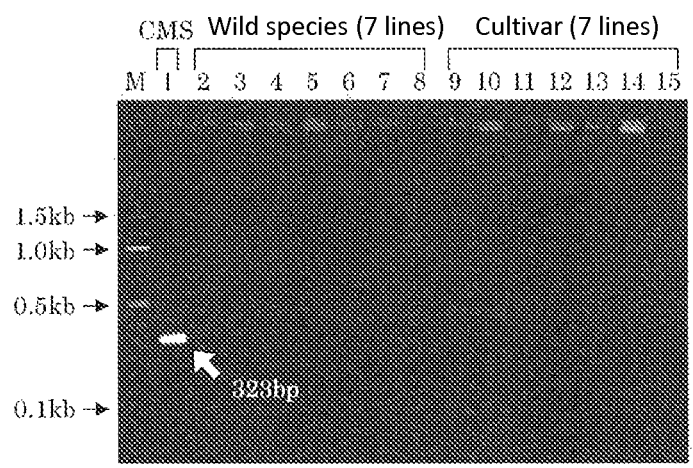
FIG. 2 shows results of electrophoresis after PCR using, as templates, the total DNAs of the cytoplasmic male sterile *Eustoma* line (SSE-CMS cytoplasm: lane 1), wild *Eustoma* species (lanes 2 to 8) retained by Sakata Seed Corporation, and *Eustoma* cultivars (lanes 9 to 15) bred by Sakata Seed Corporation. The lane M indicates a molecular weight marker reference.
Figure 2:
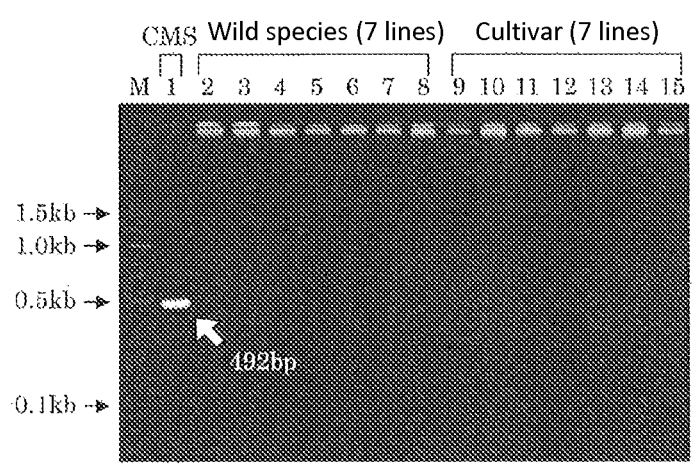
Figure 2:
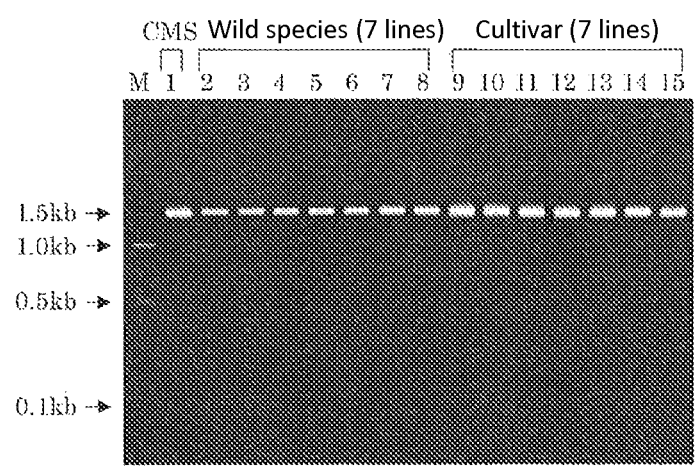

Consensus primers for mitochondrial DNA described in Non Patent Literature 5 were used to carry out PCR analysis with the SSE-CMS *Eustoma* line and an existing *Eustoma* line as templates. As a result, markers differing in the sizes of the amplified DNA fragments were found. Two types of markers, i.e., nad4L/orf25 and nad7/4-5, were selected from among such polymorphic markers, and the nucleotide sequences of the amplified fragments were analyzed. As a result, regions specific for the SSE-CMS *Eustoma* line were identified. In order to use these regions as distinctive factors, primers shown in Table 2 were designed, and PCR analysis (30 repetitive cycles each involving thermal denaturation at 94° C. for 1 minute, annealing at 65° C. for 1 minute, and elongation reaction at 72° C. for 1 minute) was carried out.

the test results are shown in FIG. 2. The experiments of FIGS. 2(A) to 2(C) were conducted under the following conditions:

FIG. 2(A): Marker 1: Marker Specific for SSE-CMS *Eustoma* Line

The nucleotide sequence (323 bp) represented by SEQ ID NO: 1 was amplified by PCR (30 cycles each involving thermal denaturation at 94° C. for 1 minute, annealing at 65° C. for 1 minute, and elongation reaction at 72° C. for 1 minute) using primers orf25-F and orf25-R.

FIG. 2(B): Marker 2: Marker Specific for SSE-CMS *Eustoma* Line

The nucleotide sequence (492 bp) represented by SEQ ID NO: 2 was amplified by PCR (30 cycles each involving thermal denaturation at 94° C. for 1 minute, annealing at 65° C. for 1 minute, and elongation reaction at 72° C. for 1 minute) using primers nad7-F and nad7-R.

FIG. 2(C): nad5/4-5: Marker Common to All *Eustoma* Plants

DNA fragments of approximately 1.5 kb were amplified from all lines by PCR (30 cycles each involving thermal denaturation at 94° C. for 1 minute, annealing at 60° C. for 1 minute, and elongation reaction at 72° C. for 1 minute) using primers nad5/4 and nad5/5.

Consequently, the SSE-CMS *Eustoma* line produced by the present invention was shown to differ from conventionally known *Eustoma* plants.

TABLE 2

Primers used in the present invention and their nucleotide sequences

| Marker name | Primer name | Nucleotide sequence (5'→3') |
|---|---|---|
| nad4L/ orf25 | orf25 (SEQ ID NO: 7) | CTGTYTTTTCGCACTTAGGC |
| | nad4L (SEQ ID NO: 8) | GTCCGRGGTACTATTGCTGT |
| nad7/4-5 | nad7/4 (SEQ ID NO: 9) | TGTCCTCCATCACGATVTCG |
| | nad7/5 (SEQ ID NO: 10) | CCAAATTCTCCTTTAGGTGC |
| Marker1 (SEQ ID NO: 1) | orf25-F (SEQ ID NO: 3) | CTACTGAATCCAAGCGAGTGG |
| | orf25-R (SEQ ID NO: 4) | TAGGTAGAGCTGGGCGAGAA |
| Marker2 (SEQ ID NO: 2) | nad7-F (SEQ ID NO: 5) | AACCACTAACACCTTCCTCGT |
| | nad7-R (SEQ ID NO: 6) | GCTCTATCTACGTATCTTG-AAGTTTC |
| nad5/4-5 | nad5/4 (SEQ ID NO: 11) | CCAATTTTTGGGCCAATTCC |
| | nad5/5 (SEQ ID NO: 12) | CATTGCAAAGGCATAATGAT |

Example 5

Callus Induction, Growth, and Redifferentiation of SSE-CMS *Eustoma* Line

In order to asexually propagate, by tissue culture, the SSE-CMS *Eustoma* line prepared by the present invention, the leaf disc of the SSE-CMS *Eustoma* line cultivated in a greenhouse was collected. The surface of leaf disc was sterilized for 10 minutes using a 1% sodium hypochlorite solution and rinsed with sterile water. The sterilized leaf disc was placed to an MS medium supplemented with 1.5 mg/l NAA to induce a callus. The callus was transferred to a B5 medium supplemented with 0.5 mg/l GA3 and 1.5 mg/l BA to induce a shoot. The formed shoot was transferred to a plant hormone-free B5 medium for rooting to regenerate a plant, which was then confirmed to be male sterile.

The callus prepared by the method described above was internationally deposited with National Institute of Technology and Evaluation (NITE) International Patent Organisms Depositary (Tsukuba Central 6, 1-1-1 Higashi, Tsukuba, Ibaraki, Japan) on Jul. 26, 2012 (indication given by the depositor for identification: 12S-134C; Deposition No. FERM BP-11507).

INDUSTRIAL APPLICABILITY

Use of the novel *Eustoma* having cytoplasmic male sterility, provided by the present invention, achieves breeding a *Eustoma* plant and its F1 variety with excellent seed productivity, flower shelf life, and/or ornamental characteristics and the producing high-quality seeds of its F1 variety.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "PS38-9001_SequenceListing.txt", created Mar. 17, 2015, file size of 4,096 bytes, is hereby incorporated by reference.

The invention claimed is:

1. A *Eustoma grandiflorum* plant having cytoplasmic male sterility, or *Eustoma grandiflorum* progeny thereof, wherein the *Eustoma grandiflorum* plant or *Eustoma grandiflorum* progeny thereof has the nucleotide sequence represented by SEQ ID NO: 1 or 2.

2. The *Eustoma* plant or progeny thereof according to claim 1, wherein the *Eustoma* plant or progeny thereof is a cytoplasmic male sterile plant produced from a cross pollination whose seed parent is a *Eustoma grandiflorum* plant having the nucleotide sequence represented by SEQ ID NO: 1 or 2, and whose pollen parent is *Eustoma grandiflorum*.

3. A partial plant body of the *Eustoma* plant or progeny thereof according to claim 1.

4. A seed of the *Eustoma* plant or progeny thereof according to claim 1.

5. A callus comprising cells of the *Eustoma* plant or progeny thereof according to claim 1.

6. A *Eustoma grandiflorum* plant that is induced from the callus according to claim 5 and asexually propagated by tissue culture, or *Eustoma grandiflorum* progeny thereof; wherein the induced plant or progeny thereof comprises SEQ ID NO: 1 or 2.

7. A partial plant body of the *Eustoma* plant or progeny thereof according to claim 6.

8. A method for preparing a *Eustoma* plant that is induced from the callus according to claim 5 and asexually propagated by tissue culture, comprising the steps of:
   transferring the callus to a redifferentiation medium;
   culturing the callus to induce a shoot; and
   transferring the shoot to a rooting medium to induce rooting.

9. A *Eustoma* plant having cytoplasmic male sterility which is designated by Deposition No FERM BP-11506, or *Eustoma grandiflorum* progeny thereof.

10. A partial plant body of the *Eustoma* plant or progeny thereof according to claim 9.

11. A seed of the *Eustoma* plant or progeny thereof according to claim 9.

12. A callus of a *Eustoma* plant having cytoplasmic male sterility which is designated by Deposition No FERM BP-11507.

13. A *Eustoma* plant that is induced from the callus according to claim 12 and asexually propagated by tissue culture, or *Eustoma grandiflorum* progeny thereof; wherein the induced plant or progeny thereof comprises SEQ ID NO: 1 or 2.

14. A partial plant body of the *Eustoma* plant or progeny thereof according to claim 13.

15. A method of preparing a *Eustoma* plant that is induced from the callus according to claim 12 and asexually propagated by tissue culture, comprising the steps of:
transferring the callus to a redifferentiation medium;
culturing the callus to induce a shoot; and
transferring the shoot to a rooting medium to induce rooting.

16. A method for producing a first filial generation seed, comprising crossing the *Eustoma grandiflorum* plant or progeny thereof according to claim 1 as a seed parent, with a *Eustoma grandiflorum* plant capable of being crossed with the seed parent plant as a pollen parent, and producing a first filial generation seed from the seed parent thus crossed.

17. A method for producing a first filial generation seed, comprising crossing the *Eustoma* plant or progeny thereof according to claim 9 as a seed parent, with a *Eustoma grandiflorum* plant capable of being crossed with the seed parent plant as a pollen parent, and producing a first filial generation seed from the seed parent thus crossed.

18. A method for producing a first filial generation seed, comprising crossing a *Eustoma* plant regenerated from the callus according to claim 12, or *Eustoma grandiflorum* progeny thereof, as a seed parent; with a *Eustoma grandiflorum* plant capable of being crossed with the seed parent plant as a pollen parent; and producing a first filial generation seed from the seed parent thus crossed.

19. A first filial generation seed produced by the method according to claim 16.

20. A first filial generation plant grown from the first filial generation seed according to claim 19.

21. A method for producing a *Eustoma* plant according to claim 1, the *Eustoma* plant having a useful character and expressing cytoplasmic male sterility, comprising the step of:
successively back-crossing a *Eustoma grandiflorum* plant having the nucleotide sequence represented by SEQ ID NO: 1 or 2 in its cytoplasm with a *Eustoma grandiflorum* plant having the useful character, to produce the *Eustoma* plant having the useful character and expressing cytoplasmic male sterility.

22. A method for producing a *Eustoma* plant according to claim 1, the *Eustoma* plant having a useful character and expressing cytoplasmic male sterility, comprising the step of:
successively back-crossing a *Eustoma* plant having cytoplasmic male sterility which is designated by Deposition No FERM BP-11506, or *Eustoma grandiflorum* progeny thereof; with *Eustoma grandiflorum* plant having the useful character; to produce the *Eustoma* plant having the useful character and expressing cytoplasmic male sterility.

23. A method for producing a *Eustoma* plant according to claim 1, the *Eustoma* plant having a useful character and expressing cytoplasmic male sterility, comprising the step of:
successively back-crossing a *Eustoma* plant that is induced from a callus of a *Eustoma* plant having cytoplasmic male sterility which is designated by Deposition No FERM BP-11507 and asexually propagated by tissue culture, or *Eustoma grandiflorum* progeny thereof; with a *Eustoma grandiflorum* plant having the useful character; to produce the *Eustoma* plant having the useful character and expressing cytoplasmic male sterility; wherein the induced plant or progeny thereof comprises SEQ ID NO: 1 or 2.

24. A *Eustoma* plant produced by the method according to claim 21, or *Eustoma grandiflorum* progeny thereof.

25. A partial plant body of the *Eustoma* plant or progeny thereof according to claim 24.

26. The *Eustoma* plant or *Eustoma grandiflorum* progeny thereof according to claim 1, having the same mitochondrial genome as a *Eustoma* plant having cytoplasmic male sterility which is designated by Deposition No FERM BP-11506, or *Eustoma grandiflorum* progeny thereof.

27. The *Eustoma* plant or progeny thereof according to claim 26, wherein the *Eustoma* plant or progeny thereof has the nucleotide sequence represented by SEQ ID NO: 1 or 2 in its mitochondrial genome.

* * * * *

UNITED STATES PATENT AND TRADEMARK OFFICE
CERTIFICATE OF CORRECTION

| | | |
|---|---|---|
| PATENT NO. | : 9,504,215 B2 | Page 1 of 1 |
| APPLICATION NO. | : 14/431913 | |
| DATED | : November 29, 2016 | |
| INVENTOR(S) | : Mori et al. | |

It is certified that error appears in the above-identified patent and that said Letters Patent is hereby corrected as shown below:

In the Claims

Column 20, Line 17: the text "thereof; with" should read -- thereof; with a --.

Signed and Sealed this
Twenty-first Day of February, 2017

Michelle K. Lee
*Director of the United States Patent and Trademark Office*